(12) United States Patent
Boese et al.

(10) Patent No.: US 7,899,223 B2
(45) Date of Patent: Mar. 1, 2011

(54) METHOD AND DEVICE FOR GENERATING A THREE-DIMENSIONAL IMAGE DATA RECORD OF A MOVING OBJECT BY MEANS OF X-RAY TOMOGRAPHY

(75) Inventors: Jan Boese, Eckental (DE); Günter Lauritsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 862 days.

(21) Appl. No.: 11/238,552

(22) Filed: Sep. 29, 2005

(65) Prior Publication Data

US 2006/0067459 A1    Mar. 30, 2006

(30) Foreign Application Priority Data

Sep. 30, 2004    (DE) .................. 10 2004 048 209

(51) Int. Cl.
*G06K 9/00*    (2006.01)
*A61B 6/00*    (2006.01)
(52) U.S. Cl. ............................. 382/128; 378/4
(58) Field of Classification Search .................. 382/128, 382/131, 174, 285; 378/4
See application file for complete search history.

(56) References Cited

U.S. PATENT DOCUMENTS

| | | | |
|---|---|---|---|
| 6,486,671 B1 * | 11/2002 | King | 324/307 |
| 2004/0120446 A1 * | 6/2004 | Londt et al. | 378/4 |
| 2004/0175024 A1 | 9/2004 | Rasche et al. | |
| 2004/0258296 A1 * | 12/2004 | Bruijns | 382/154 |
| 2006/0188135 A1 * | 8/2006 | Zarkh et al. | 382/128 |

FOREIGN PATENT DOCUMENTS

| | | |
|---|---|---|
| DE | 101 29 631 A1 | 1/2003 |
| WO | WO 2004/081877 A1 | 9/2004 |

OTHER PUBLICATIONS

Blondel, C., Vaillant, R., Malandain, G., & Ayache, N. (2004). 3D tomographic reconstruction of coronary arteries using a precomputed 4D motion field. Physics in Medicine and Biology, 49(11), 2197-2208.*

(Continued)

*Primary Examiner* — John B Strege
*Assistant Examiner* — Nirav G Patel (57) ABSTRACT

A precise and comparatively simple method for generating a three-dimensional image data record of a moving object using X-ray tomography and a device that is particularly suitable for implementing the method with an X-ray emitter/detector unit supported such that it can be rotated and with an evaluation unit are specified. According to the invention a number of two-dimensional raw images are grouped according to a cyclical relative time, at least two preliminary 3D image data records respectively are generated from raw images that correspond to one another according to this grouping, at least one movement matrix is derived by comparing two preliminary 3D image data records used as the source data record and the target data record respectively, a 3D image data record with compensation for movement corresponding to a reference time of the source data record is generated by applying the or each movement matrix to the associated target data record and the or each 3D image data record with compensation for movement is added to at least one further 3D image data record with compensation for movement or to another preliminary 3D-image data record corresponding to the same reference time.

8 Claims, 4 Drawing Sheets

OTHER PUBLICATIONS

Shechter, G., Devernay, F., Maniere, E. C., & Mcveigh, E. R. (2002). Temporal tracking of 3D coronary arteries in projection angiograms. , 4684(1) 612-623.*

W. Chlewicki: "3D Simultaneous Algebraic Reconstruction Technique for Cone- Beam Projections"; Master's Thesis, University of Patras, 2001.*

Shechter, G., Devernay, F., Maniere, E. C., & Mcveigh, E. R. (2002). Temporal tracking of 3D coronary arteries in projection angiograms. , 4684(1).*

Schäffter T, Rasche V, Carlsen IC. "Motion compensated projection reconstruction". Magn Reson Med 1999;41:954-963.*

Christophe Blondel, Grégoire Malandain, Régis Vaillant, Nicholas Ayache; "4D Deformation Field of Coronary Arteries from Monoplane Rotational X-Ray Angiography"; International Congress Series 1256 (2003); pp. 1073-1078; Elsevier Science B.V.

Christophe Blondel, Grégoire Malandain, Régis Vaillant, Frédéric Devernay, Éve Coste-Manière, and Nicholas Ayache; "4D Tomographic Representation of Coronary Arteries from One Rotational X-Ray Sequence"; MICCAI 2003, pp. 416-423; LNCS 2878; Springer-Verlag Berlin Heidelberg.

O. Wink, R. Kemkers, S.J. Chen, and J.D. Carroll; "Coronary Interention Planning Using Hybrid 3D Reconstruction"; MICCAI 2002; pp. 604-611; LNCS 2488, Springer-Verlag Berlin Heidelberg.

* cited by examiner

METHOD AND DEVICE FOR GENERATING A THREE-DIMENSIONAL IMAGE DATA RECORD OF A MOVING OBJECT BY MEANS OF X-RAY TOMOGRAPHY

CROSS REFERENCE TO RELATED APPLICATIONS

This application claims priority to the German application No. 10 2004 048 209.8, filed Sep. 30, 2004, filed Sep. 30, 2004 which is incorporated by reference herein in its entirety.

FIELD OF INVENTION

The invention relates to a method for generating a three-dimensional image data record of a moving object by means of X-ray tomography. The invention also relates to a device for implementing said method. X-ray tomography generally refers to an imaging X-ray method for generating a three-dimensional image data record (tomogram) of an object. The term X-ray tomography here includes both conventional computed tomography and in particular also so-called 3D rotational angiography.

BACKGROUND OF INVENTION

Angiography generally refers to the representation of the blood vessels, in particular the arteries, veins and ventricles of the (generally human) body by means of imaging X-ray methods. With 3D rotational angiography, as with computed tomography, a number of two-dimensional X-ray images (raw images) of a patient are recorded at different recording projections. These raw images are then used to generate a three-dimensional image data record of the blood vessels to be examined. In particular when examining the heart and the coronary arteries surrounding it, it is problematic for recording purposes that these blood vessels are subject to constant movement as a result of the heartbeat. Such movement generally results in significant image artifacts when the 3D image data record is reconstructed, significantly impairing the quality of said image data record.

SUMMARY OF INVENTION

Until now such movement artifacts were reduced during 3D rotational angiography of the heart and blood vessels in proximity to the heart using a method referred to as ECG gating. With such a method, as for example known from O. Wink et al. "Coronary Intervention Planning, Using Hybrid 3D Reconstruction", MICCAI 2002, LNCS 2488 (Springer), pages 604-611, 2002, the raw images are synchronized with the cardiac rhythm of the patient by means of an ECG signal, with only the raw images recorded during a predefined low-movement phase of the cardiac cycle being used to reconstruct the 3D image data record. However this results in a significant reduction in the number of useable raw images. Thus when using ECG gating only a few raw images can be used from the generally several hundred raw images recorded during a full rotation of the X-ray emitter/detector unit of a 3D rotational angiography unit. This reduction in the number of images in turn results in a significant deterioration in image quality both in respect of spatial resolution and contrast resolution.

Methods are also known from Ch. Blondel, et al., "4D-Deformation Field of Coronary Arteries from Monoplane Rotational X-Ray Angiography", Internat. Congress Ser. 1256 (Elsevier), pages 1073-1087, 2003 and Ch. Blondel, et al. "4D-Tomographic Representation of Coronary Arteries from One Rotational X-Ray Sequence", MICCAI 2003, LNCS 2878 (Springer), pages 416-423, 2003, with which the image quality of a tomographic representation of the coronary arteries is further improved by compensating for arterial movement. These methods are based on segmentation of the coronary arteries from the raw images recorded at a specific point of the cardiac cycle, modeling of the movement of the coronary arteries based on a 3D point model of the coronary artery tree obtained from this segmentation and then production of a tomogram with compensation for deformation from the raw images. Such a method is disadvantageously associated with a comparatively high numerical outlay.

A method for reconstructing a high-resolution 3D image is known from DE 101 29 631 A1, according to which preliminary 3D image data records are generated from grouped raw images, from which movement information in 3D space is obtained.

A method for reconstructing 3D volume images with compensation for movement is disclosed in WO 2004/081877 A1, in which movement is compensated for in 2D images and these are then used to generate a 3D image.

An object of the invention is to specify a method and a device which allow for the generation of a top-quality three-dimensional image data record of a moving object by means of X-ray tomography in a comparatively simple manner.

This object is achieved by the claims.

According to this the device according to the invention comprises an X-ray emitter/detector unit, which is supported on a C-arm, etc. such that it can be rotated preferably about an isocentric axis, so that the X-ray emitter/detector unit can be used to record raw images of an object located approximately in the isocenter at different projection angles. The object is a patient to be examined or a part of the body of the same in particular. The device also comprises an evaluation unit to generate a three-dimensional image data record of the object based on the raw images recorded.

To this end the raw images are first synchronized according to a cyclical relative time, i.e. divided into groups with comparable relative time. Relative time here refers to a reference variable that varies over time cycles, which is in some instances preferably derived from the cardiac cycle of the patient.

At least two such groups of raw images are used in each instance to generate an associated preliminary 3D image data record, which corresponds accordingly to a point of relative time in each instance (referred to below as the reference time). A 3D image data record refers to a three-dimensional field of image elements (voxels), with a color value or gray-scale value assigned to each. 3D reconstruction methods, in particular a filtered back-projection method, as deployed in conventional 3D rotational angiography, are used to generate the preliminary 3D image data records from the two-dimensional raw images.

An associated movement matrix is now derived by comparing two such preliminary 3D image data records. A movement matrix refers to a three-dimensional vector field, by means of which voxels or voxel groups of the one 3D image data record are linked to voxels or voxel groups of the other 3D image data record. The movement matrix hereby describes a "movement", i.e. a spatial change in mutually corresponding image structures from the first 3D image data record (source data record) used as the starting point to the temporally later or earlier second 3D image data record (target data record). The movement matrix is preferably produced from the source data record and the target data record by means of a correlation method, e.g. block matching or a method based on optical flow.

It is then possible to simulate temporal backward development (or forward development) of the image information in the target data record by subsequently applying the or each movement matrix to the associated target data record. The result of this operation is a 3D image data record with compensation for movement, which corresponds to the reference time of the associated source data record.

The or each 3D image data record with compensation for movement is then added to each further 3D image data record with compensation for movement corresponding to the same reference time. The addition operation alternatively or additionally includes at least one preliminary 3D image data record corresponding to the same reference time, in particular the associated source data record.

The method described above can be implemented automatically with comparatively little outlay and in particular allows an extremely precise three-dimensional representation of the human blood vessels in proximity to the heart. Correlating two preliminary 3D image data records to produce the movement matrix involves comparatively little numerical outlay and is relatively stable. The method can also be implemented even when no clearly segmentable structures are present or can be identified in the 3D image data records used as the source or target data record.

In a preferred embodiment of the method and the associated device, before deriving the or each matrix, the preliminary 3D image data records used to this end are pretreated using electronic image processing means, in particular contrast smoothing and gray-scale value or color value fenestration. This suppresses noise effects and reconstruction artifacts that are present in the preliminary 3D image data records to a relatively significant degree.

A further improvement in image quality can optionally be achieved by regularizing the or each movement matrix. Regularization in this sense refers to any method that allows homogenization, noise and artifact suppression, etc. in a vector field, in particular smoothing methods in location and time domains, fenestration methods, etc. Regularization is preferably parameterized on the basis of stored information about typical movement patterns of the object. Threshold values for fenestration of the movement matrix are in particular preferably derived from experiential values for the spatial amplitude of arterial movement in the human body and cardiac frequency. In this manner it is possible in particular to identify atypically extensive or rapid structural changes in the movement matrix—that cannot be reconciled with arterial movement due to the heartbeat—as artifacts and to remove them from the movement matrix.

The relative time is derived in particular from the cardiac cycle of the patient to be examined, by taking a saw-tooth type function synchronized with the cardiac cycle as the relative time. The cardiac cycle is thereby measured in particular by means of an ECG unit and supplied as an ECG signal. Alternatively the cardiac cycle can be estimated from the recorded raw images, e.g. by subjecting the image information in the raw images to a temporal spectral analysis, a regressive adaptation method, etc.

To produce the preliminary 3D image data records the relative time is preferably first divided into a number of equal time windows, the raw images assigned to the same time window being used in each instance as the basis for a preliminary 3D image data record.

BRIEF DESCRIPTION OF THE DRAWINGS

Exemplary embodiments of the invention are described in more detail below with reference to a drawing, in which.

Corresponding parts and variables are assigned the same reference characters in all the figures.

DETAILED DESCRIPTION OF INVENTION

Figure 1:
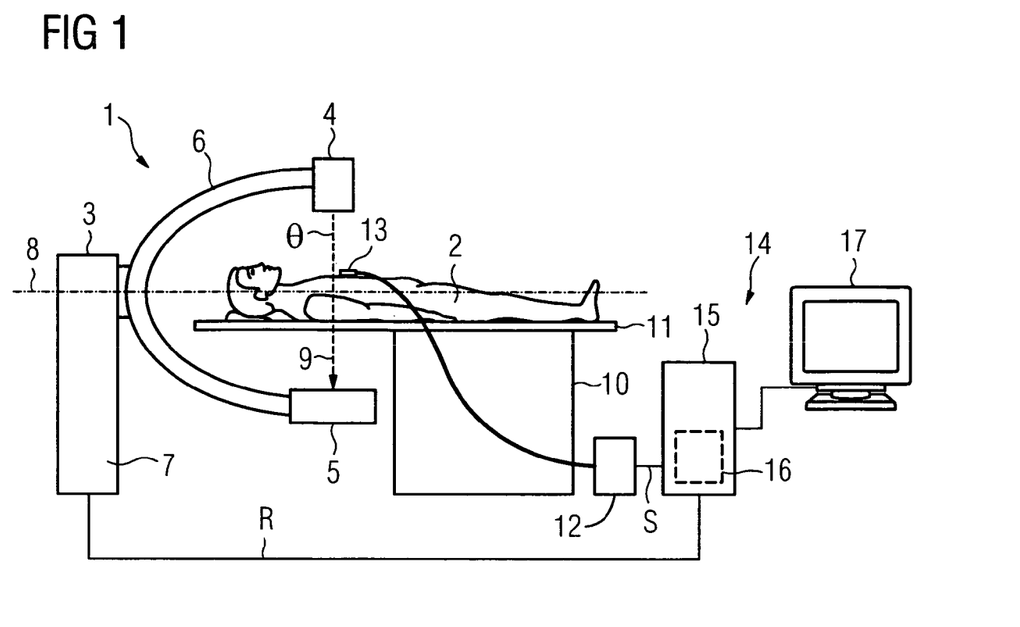
FIG. 1 shows a schematic diagram of a 3D rotational angiography unit (X-ray tomograph) with a patient support, with an X-ray emitter/detector unit that can be rotated about said support and with a control and evaluation system.

FIG. 1 shows a schematic diagram of a device 1 for generating a three-dimensional image data record of an object. The device 1 is an X-ray tomograph, in particular a 3D rotational angiography unit. The object to be examined is a patient 2, in particular the chest area of a patient 2.

The device 1 comprises a recording unit 3 with an X-ray emitter 4 and an X-ray detector 5. The X-ray emitter 4 and X-ray detector 5 are opposite each other at the ends of a so-called C-arm 6. The C-arm 6 is in turn supported roughly in the center on a stand 7 such that it can be rotated about an isocentric axis 8. The X-ray emitter 4 and X-ray detector 5 can thereby be twisted in relation to the stand 7 by pivoting the C-arm 6 such that a central beam 9 of the X-ray radiation emitted by the X-ray emitter 4 towards the X-ray detector 5 can be swung at any projection angle θ in relation to the surrounding space within a recording plane perpendicular to the isocentric axis 8, the central beam 9 always being directed toward the isocentric axis 8. The position of the recording unit 3 shown in FIG. 1, in which the central beam 9 is directed vertically from top to bottom, corresponds to a projection angle of θ=0°.

The device 1 also comprises a patient table 10 with a table top 11, on which the patient 2 is supported during an examination, such that the longitudinal axis of the body is roughly aligned with the isocentric axis 8 of the recording unit 3. The table top 11 can be inserted into the opening of the C-arm 6 for examination purposes such that the area of the body of the patient 2 to be examined is located between the X-ray emitter 4 and the X-ray detector 5.

The device 1 also comprises an ECG unit 12 with a number of ECG sensors 13, which are attached in the known manner to the body of the patient 2 to record an electrocardiogram (ECG), i.e. an electrical signal reflecting the cardiac activity of the patient 2.

The device 1 also comprises a control and evaluation system 14. The control and evaluation system 14 comprises a data processing unit 15, in which in addition to operating and control functions (not shown in more detail) there is an evaluation unit 16 to generate a three-dimensional (3D) image data record of the area of the body of the patient 2 being examined. The control and evaluation system 14 also comprises input/output means 17, e.g. screen, keyboard, mouse, etc. for inputting control instructions and for displaying status variables, examination results, etc.

During the course of the method implemented by the device 1 the recording unit 3 feeds digital image data of two-dimensional X-ray images, hereafter referred to as raw images R, to the evaluation unit 16. An ECG signal S from the patient 2 is also fed to the evaluation unit 16 by the ECG unit 12.

Figure 2:
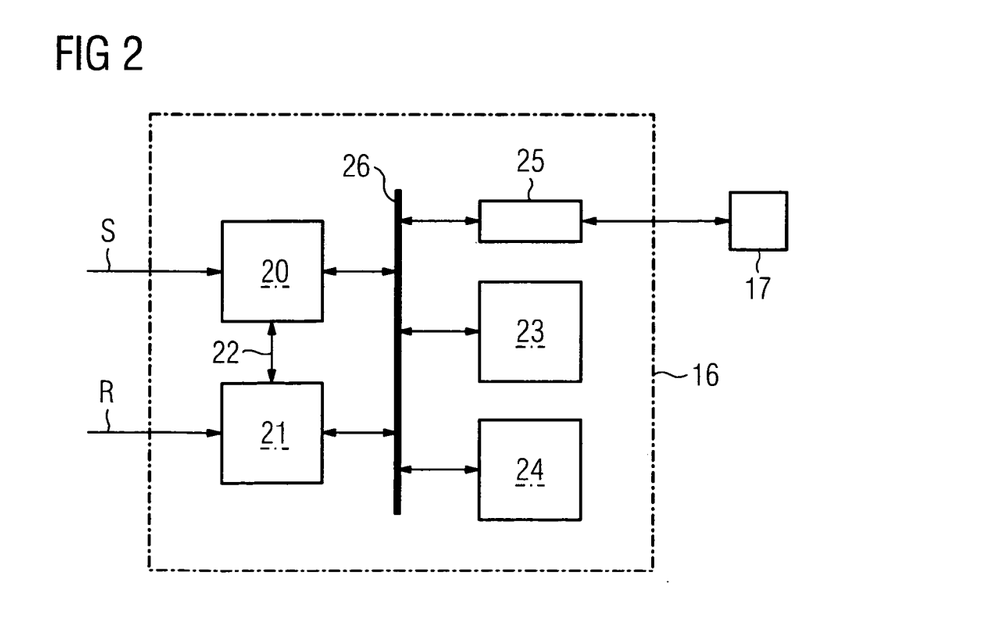
FIG. 2 shows a schematic block circuit diagram of an evaluation unit in the control and evaluation system according to FIG. 1.

The structure of the evaluation unit 16 is shown in more detail in FIG. 2. According to this the evaluation unit 16 has an input interface 20 for the ECG signal S and a further input interface 21 for the image data corresponding to the raw images R. The input interfaces 20, 21 are synchronized with each other by means of a synchronization connection 22 such that a temporally corresponding point of the ECG signal S can be assigned to each raw image R.

The evaluation unit 16 also comprises an analysis module 23, in which algorithms are implemented to process and modify the raw images R and the ECG signal S according to the method described in more detail below. To store the raw images R, the ECG signal S and data supplied as described in more detail below, the evaluation unit 16 also has a storage module 24. The evaluation unit 16 also has an input/output interface 25 for data communication with the input/output means 17. The input interfaces 20, 21, the analysis module 23, the storage module 24 and the input/output interface 25 are provided by hardware components of the data processing unit 15 and associated software and exchange data bilaterally via a common bus system 26.

Figures 3, 4:
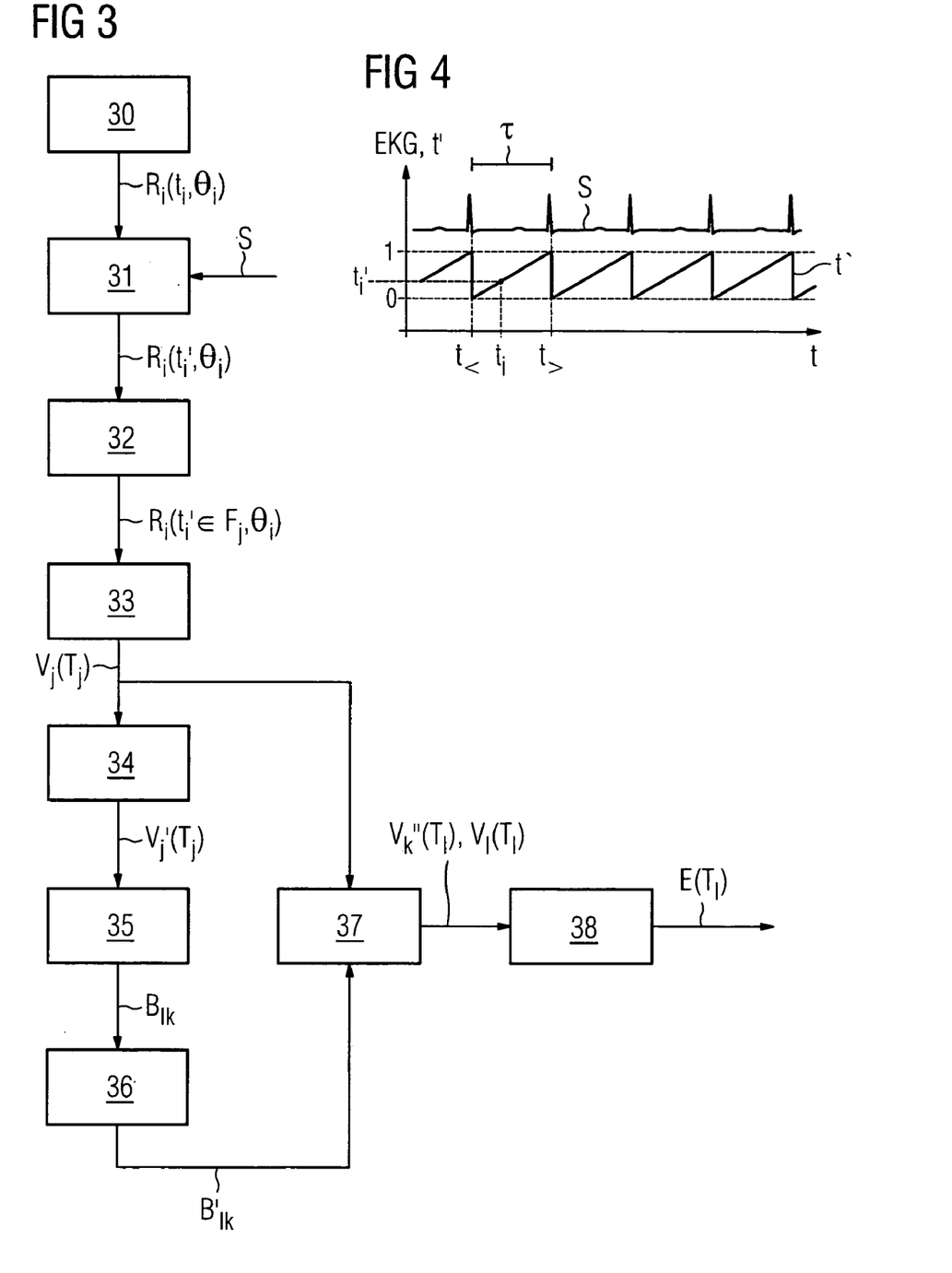
FIG. 3 shows a schematic flow diagram of a method that can be implemented using the X-ray tomograph according to FIG. 1, to generate a three-dimensional image data record, with the method steps raw image recording, raw image synchronization, raw image grouping (ECG gating), back-projection, data pretreatment, movement detection, data posttreatment, compensation for movement and data accumulation.
FIG. 4 shows a schematic diagram of an ECG signal over time and a cyclical relative time derived therefrom for the method according to FIG. 3.

According to FIG. 3 the method implemented using the device 1 comprises the method steps raw image recording 30, raw image synchronization 31, raw image grouping or ECG gating 32, filtered back-projection 33, data pretreatment 34, movement detection 35, data posttreatment 36, compensation for movement 37 and data accumulation 38.

During the course of raw image recording 30, with the recording unit 3 rotating, a number of typically several hundred raw images R are recorded during one rotation of the C-arm 6 through an angle range of typically more than 180°. Each individual raw image $R_i$ (i=1, 2, 3, ..., N) is hereby characterized by a recording time $t_i$ and a projection angle $\theta_i$, expressed below by the functional notation $R_i(t_i,\theta_i)$. Each raw image $R_i$ comprises a two-dimensional data field of image points (pixels), with a gray-scale or color value assigned to each.

During the course of raw image synchronization 31 a so-called cyclical relative time t' is first determined based on the ECG signal S. A variable between 0 and 1 is taken as the relative time t', varying in a saw-tooth manner and therefore in particular periodically with the recording time t. The period duration τ of the relative time t' is thereby tailored to the periodicity of the ECG signal S. As shown in FIG. 4, the relative time $t_i'$ assigned to any recording time $t_i$ of a raw image $R_i$ can be determined by the formula $$\text{a. } t_i' = \frac{t_i - t_<}{t_> - t_<} \quad \text{EQU 1}$$

with $t_<$ and $t_>$ designating the times indicated by the so-called R deflection of the ECG signal, which represent the start and end of the current cardiac phase. During the course of raw image synchronization 31 the recording time $t_i$ is therefore mapped onto the corresponding relative time $t_i'$.

Figure 5:
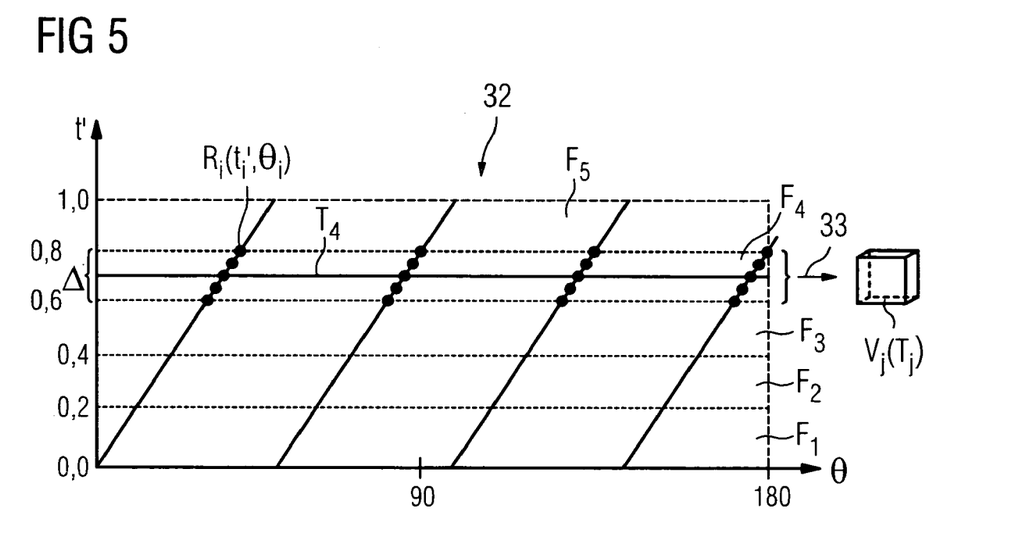
FIG. 5 shows a schematic diagram of the principles of raw image grouping and back-projection during the method according to FIG. 3.

During subsequent ECG gating 32 the raw images $R_i(t_i',\theta_i)$ are grouped according to the relative time t'. The relative time t' is hereby divided into a number of time windows $F_j$ (j=1, 2, ..., M), each being assigned a mean relative time as the reference time $T_j$ and a width Δ. The time windows $F_j$ are in particular selected such that temporally they are immediately adjacent to each other (FIG. 5). The following thereby applies for the reference times $T_j$ $$\text{a. } T_j = \frac{j - 1/2}{M}, \quad \text{EQU 2}$$

where j=1, 2, ..., M. $\Delta = M^{-1}$ applies for the width Δ. Alternatively however the width Δ can also be greater, so that adjacent time windows $F_j$ overlap. The raw images $R_i$ in the respective time window $F_j$ can also be weighted such that for example raw images $R_i$ at the edges of the time window $F_j$ are smoothed to zero.

All the raw images $R_i(t_i' \in F_j, \theta_i)$ assigned to a given time window $F_j$ are grouped, i.e. selected. Filtered back-projection 33 is then used to generate a preliminary 3D image data record $V_j$ from these grouped raw images $R_i$. Back-projection takes place according to a standard method, in particular the Feldkamp method. The resulting preliminary 3D image data record $V_j$ therefore corresponds to the reference time $T_j$.

The ECG gating 32 described by way of an example in FIG. 5 with reference to the time window $F_4$ and the subsequent back-projection 33 are implemented for every time window $F_j$, such that after the back-projection 33 there is an associated preliminary 3D image data record $V_j(T_j)$ for every reference time $T_j$.

As shown in FIG. 5 only raw images $R_i$ for specific segments of the projection angle θ are included in the reconstruction of a preliminary 3D image data record $V_j$ further to the ECG gating 32. As a result of this back-projection of segments, the preliminary 3D image data records $V_j$ contain artifacts which impair the spatial image information. To reduce these artefacts, the preliminary 3D image data records $V_j$ are treated during the course of data pretreatment 34 using electronic image processing means, in particular smoothing and fenestration. Voxels with a low gray-scale or color value in particular are suppressed.

As a result of the data pretreatment 34, a treated 3D image data record $V_j'$ is output for every reference time $T_j$, in which the reconstruction artifacts are suppressed, such that highly contrasting structures are more predominant in the 3D image data records $V_j'$. However due to image processing poorly contrasting structures, as produced by small secondary arteries for example, are also suppressed, such that the treated 3D image data records $V_j'$ would not be wholly suitable for diagnostic purposes.

Figure 6:
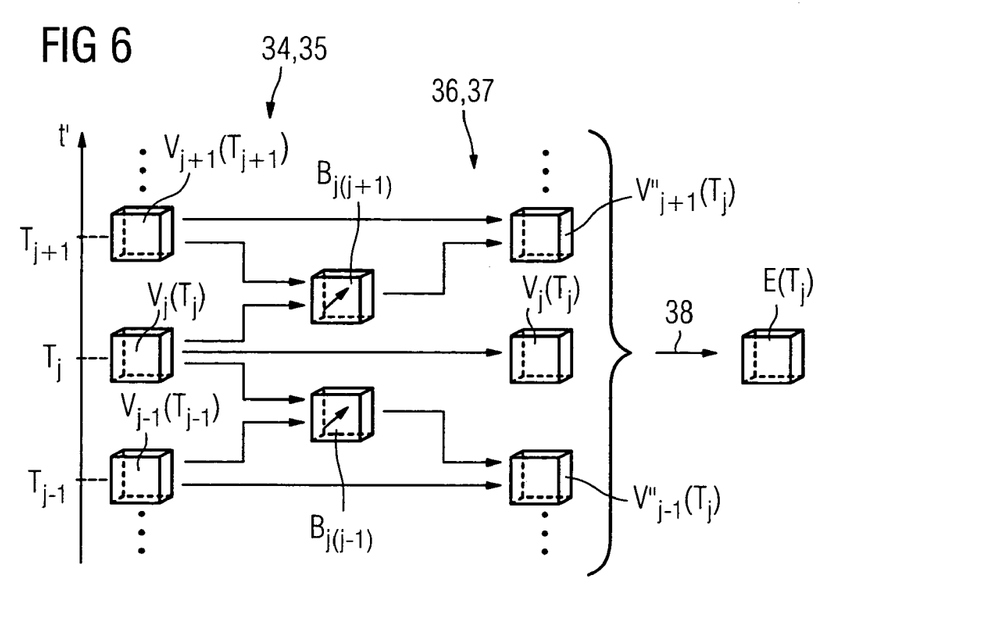
FIG. 6 shows a schematic diagram of the principles of movement detection, compensation for movement and data accumulation during the method according to FIG. 3

However contrast enhancement means that the treated 3D image data records $V_j'$ are particularly suitable for identifying structure movement between two difference reference times $T_j$. This takes place during the course of the subsequent movement detection 35, the principle of which is shown in FIG. 6. A corresponding detector module of the analysis module 23 hereby compares two treated 3D image data records $V_j'$ in respect of the spatial change in the three-dimensional image information. This is done using standard correlation methods or by determining the optical flow. As a result of movement detection 35 a number of movement matrices $B_{lk}$(l,k=1, 2, ..., M) are generated, which characterize the spatial change in the three-dimensional image information between a source data record $V_l'$ and a target data record $V_k'$. The velocity field of a structure movement can be derived from this spatial structure change taking into account the reference times $T_l$ and $T_k$ assigned to the source data record $V_l'$ and the target data record $V_k'$.

Every movement matrix $B_{lk}$ is a three-dimensional data field of 3D vectors, each establishing a correlation between a voxel or a voxel area of the source data record $V_l$ (or $V_l'$) and a voxel or voxel area of the target data record $V_k$ (or $V_k'$). In FIG. 6 for reasons of clarity only correlations between the source data record $V_j \rightarrow V_l$ and temporally adjacent target data records $V_{j-1}, V_{j+1} \rightarrow V_k$ are shown. In principle however movement matrices $B_{lk}$ for any target data records $V_k$ are preferably determined in this manner with k=1, 2, ..., M and k≠l.

The movement matrices $B_{lk}$ are now regularized during the course of data posttreatment 36, in particular smoothed in location and time domains. During regularization typical movement patterns of the coronary arteries are also taken into account. For example maxima for the vector components of the movement matrices $B_{lk}$ are estimated from the cardiac frequency of the patient 2 and the typical spatial movement amplitude of the coronary arteries in the human body and these are used to identify and eliminate artifacts within the movement matrices $B_{lk}$.

Treated movement matrices $B_{lk}'$ result from the data posttreatment 36. By applying a movement matrix $B_{lk}'$ to the associated target data record $V_k$ it is possible to develop the temporal pattern of the image information of the respective 3D image data record $V_k$ backward or forward to the reference time $T_l$ of the source data record $V_l$. It should be noted here that the or each movement matrix $B_{lk}'$ is applied not to the treated target data record $V_k'$, from which it was calculated, but to the target data record $V_k$ in its original form, to utilize all the structure information in the preliminary 3D image data records $V_j$.

The result of such an application, implemented during the course of compensation for movement 37, is a 3D image data record with compensation for movement $V_k''$, corresponding to the reference time $T_l$ of the respective source data record $V_l$. Application of the movement matrix $B_{lk}'$ to the target data record $V_k$ is expressed symbolically below by the formula $V_k''(T_l) = B_{lk}' \cdot V_k(T_k)$.

As a result of compensation for movement 37 a number of 3D image data records with compensation for movement $V_k''$ are therefore output, all of which correspond to the same reference time $T_l$, namely that of the common source data record $V_l$. The voxels of these 3D image data records with compensation for movement $V_k''(T_l)$ are added to those of the associated source data record $V_l(T_l)$ during the course of data accumulation 38. The term accumulation in this sense includes every form of summing, in particular simple summation, arithmetic averaging, weighted averaging, etc. As a result of data accumulation 38, and therefore as the end result of the method shown in FIG. 3, a final 3D image data record E is output, corresponding to the reference time $T_l$.

The effect of the method described above is based in particular on the fact that all the 3D image data records $V_k''(T_l)$ and $V_l(T_l)$ used for the data accumulation 38 correspond in respect of the image-related structure information due to the compensation for movement. All the image structures, which originate from structures in the body of the patient 2, in particular said patient's blood vessels, therefore always appear in the same place in these 3D image data records, while the reconstruction artifacts for all said 3D image data records differ. During data accumulation 38 the reconstruction artifacts are therefore averaged out while the structural image information is emphasized. In the final 3D image data record E therefore it is even possible to identify comparatively poorly contrasting structures, which are concealed by reconstruction artifacts in the preliminary image data records $V_j$.

The method according to FIG. 3 is in particular expressed by the formula $$a. \quad E(T_l) = \sum_{k=1}^{M} B_{lk}' \cdot V_k(T_k). \qquad \text{EQU 3}$$

For reasons of simplification, the sum in EQU 3 covers all k=1, 2, ..., M and therefore also formally includes a term for k=1, to which however the identity $B_{ll}' \cdot V_l(T_l) = V_l(T_l)$ commonly applies.

At every reference time $T_l$ where l=1, 2, ..., M a corresponding final 3D image data record $E_l(T_l)$ is preferably calculated such that all the four-dimensional information about the spatial arrangement of the coronary arteries in the body of the patient 2 and the changes in this arrangement over time during a cardiac cycle is available.

Figure 7:
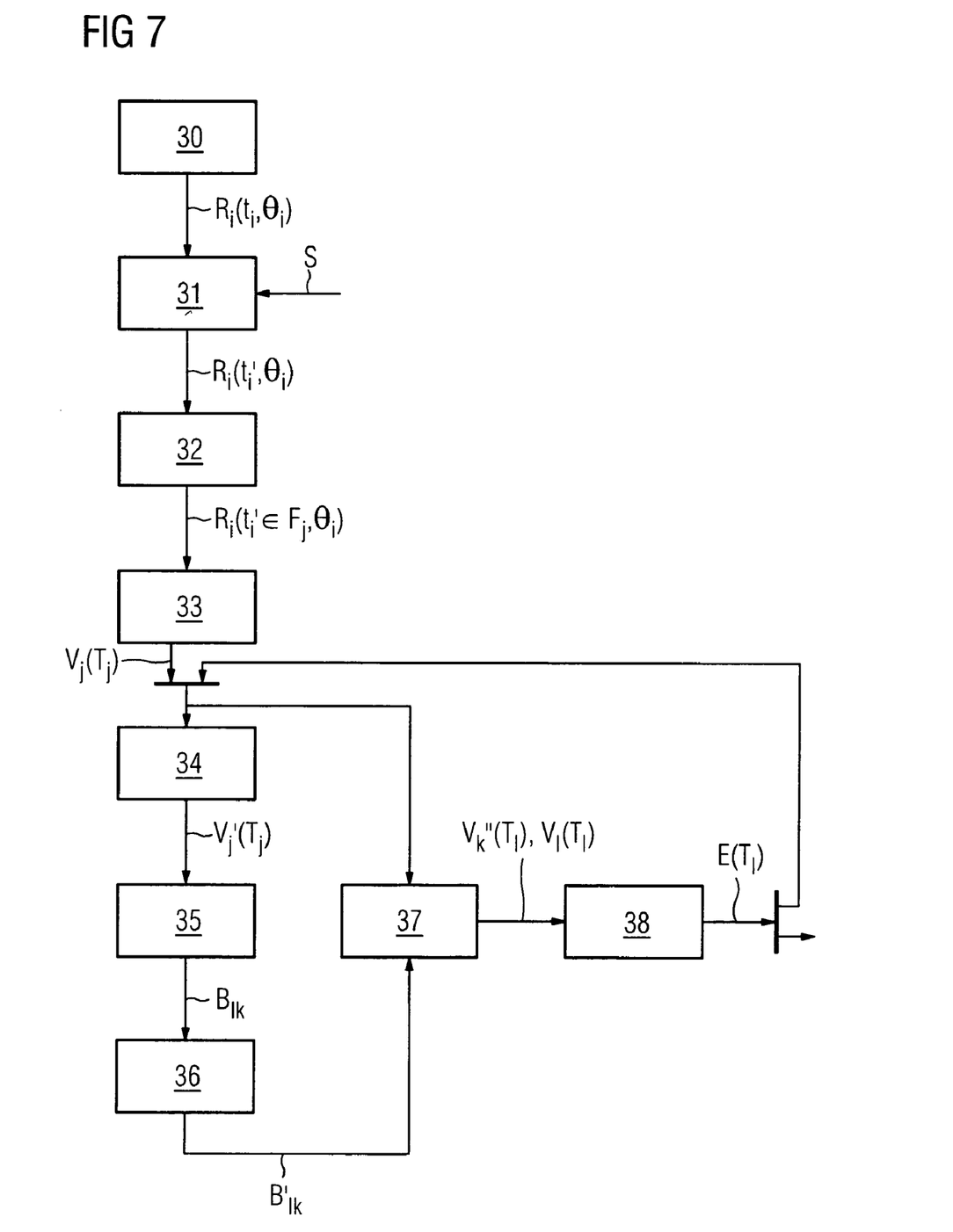
FIG. 7 shows a diagram of an iteratively implemented variant of the method according to FIG. 3.

FIG. 7 shows an iteratively implemented variant of the method described above. Here for every preliminary 3D image data record $V_j$ only adjacent image data records $V_{j-1}$ and $V_{j+1}$ are compensated for movement and added together, with the resulting 3D image data records $E_l$ being fed back into the method instead of the preliminary 3D image data records $V_j$. This iteration cycle is continued until a predefined discontinuation criterion is satisfied. An iteration step in the method variant shown in FIG. 7 is expressed by the formula $$a. \quad \sum_{k=j-1}^{j+1} B_{jk}' \cdot V_k(T_k) \rightarrow V_j(T_j) \qquad \text{EQU 4}$$

where j=1, 2, ..., M. Combinations of method variants according to FIG. 3 and FIG. 7 are optionally provided. In particular during the course of successive iteration steps compensation for movement can include an increasing number of adjacent time windows. It is also possible optionally not to determine the relative time t' based on an ECG signal S but to estimate it directly from the raw images $R_i$. To this end the change in image information in the raw images $R_i$ over time is considered and used to derive the cardiac cycle of the patient 2 by means of temporal spectral analysis, adaptation with a predefined model function or the kymogram method generally used in computed tomography.

The invention claimed is:

1. A method of generating a three-dimensional image data record of a moving object whose movement results from cardiac cycles, comprising:
   providing a device for generating three-dimensional image data records of a moving object by X-ray tomography;
   acquiring a number of two-dimensional raw images of the moving object with the device;
   grouping the two-dimensional raw images relative to a cyclical relative time period based on one or more of the cardiac cycles;
   generating at least two preliminary 3D image data records based on such raw images corresponding to each other relative to the grouping, a first of the preliminary 3D image data records acquired at a first reference time in the time period and second of the preliminary 3D image data records acquired at a second reference time in the time period where the first and second reference times differ;

determining at least one movement matrix based on the difference between the first and second reference times in the time period and based on the at least two preliminary 3D image data records, the first of the at least two preliminary 3D image data records serving as a source data record and the second of the at least two preliminary 3D image data records serving as a target data record;

determining at least one movement-compensated 3D image data record by calculating a transformation of the target data record, the transformation including mathematically operating the movement matrix upon the target data record, the movement-compensated 3D image data record corresponding to the reference time of the source data record; and adding the movement-compensated 3D image data record to at least one further movement-compensated 3D image data record corresponding to the first reference time or to a further preliminary 3D image data record corresponding to the first reference time.

2. The method according to claim 1, wherein the at least two preliminary 3D image data records are pre-processed by applying an image processing algorithm before determining the at least one movement matrix.

3. The method according to claim 2, wherein the image processing algorithm includes an algorithm chosen from the group consisting of smoothing a voxel contrast, gray-scale fenestration and color value fenestration.

4. The method according claim 1, wherein the movement matrix is regularized.

5. The method according to claim 4, wherein the movement matrix is smoothed in a location or a time domain.

6. The method according to claim 4, wherein regularizing the movement matrix is based on stored information including typical movement patterns of the moving object.

7. The method according to claim 1, wherein at least one of the cardiac cycles of the patient is determined based on an ECG signal.

8. The method according to claim 1, wherein at least one of the cardiac cycles is estimated based on the two-dimensional raw images.

* * * * *